(12) United States Patent
Smith et al.

(10) Patent No.: US 7,345,202 B2
(45) Date of Patent: Mar. 18, 2008

(54) USE OF SULFAMIC ACIDS AS RESOLVING AGENT

(75) Inventors: Alan Arthur Smith, Heemstede (NL); Franciscus Wilhelmus Petrus Damen, Nijmegen (NL); George Johannes Theodorus Kuster, Nijmegen (NL)

(73) Assignee: Avantium International B.v. (NL)

( * ) Notice: Subject to any disclaimer, the term of this patent is extended or adjusted under 35 U.S.C. 154(b) by 264 days.

(21) Appl. No.: 10/479,565

(22) PCT Filed: Jun. 7, 2002

(86) PCT No.: PCT/EP02/06321

§ 371 (c)(1),
(2), (4) Date: May 6, 2004

(87) PCT Pub. No.: WO02/100804

PCT Pub. Date: Dec. 19, 2002

(65) Prior Publication Data

US 2004/0186298 A1    Sep. 23, 2004

(30) Foreign Application Priority Data

Jun. 8, 2001    (EP) ............................... 012022513

(51) Int. Cl.
*C07C 211/00* (2006.01)
(52) U.S. Cl. ..................... 564/336; 546/339
(58) Field of Classification Search ............... 546/336, 546/343, 339; 564/336
See application file for complete search history.

(56) References Cited

U.S. PATENT DOCUMENTS

| | | | |
|---|---|---|---|
| 2,933,513 A | | 4/1960 | Nomine et al. |
| 4,582,928 A | | 4/1986 | Aoki et al. |
| 4,824,950 A | | 4/1989 | Barcza |
| 5,194,446 A | * | 3/1993 | Lo et al. ..................... 514/494 |

OTHER PUBLICATIONS

A.G Lloyd, et al.: "Preparation of 2-deoxy-2-'35S!sulphoamino-D-glucose" Biochemical Journal, vol. 92, 1964, pp. 68-72, XP001030872 Portland Press, London, GB.
S.-K. Chung, et al.: "Sytnthesis and bioactivities of steroid derivatives as antifungal agents" TETRAHEDRON, vol. 54, No. 52, Dec. 24, 1998, pp. 15899-15914, XP004144536 Elsevier Science Publishers, Amsterdam, NL.
M. L. Wolfram, et al.: "Derivatives of D-glucose containing the sulphamino group" Journal of the American Chemical Society, vol. 79, No. 18, Sep. 20, 1957, pp. 5043-5046, XP002182277 American Chemical Society, Washington, DC, US.
M.H. Payne, et al.: "Positional effects of sulphation in hirudin and hirudin PA related anticoaguant peptides" Journal of Medicinal Chemistry, vol. 34, No. 3, Mar. 1991, pp. 1184-1887, XP002182278 American Chemical Society, Washington, DC, US.
R. Cosstick, et al.: "Synthesis of some analogues of nucleoside 5'-triphosphates" TETRAHEDRON, vol. 40, No. 2, 1984, pp. 427-431, XP002182279 Elsevier Science Publishers, Amsterdam, NL.
I. Marle, et al.: "Separation of enantiomers using cellulase (CBH I) silica as a chiral stationary phase" Journal of Chromatography, vol. 586, No. 2, Nov. 22, 1991, pp. 233-248, XP002182280 Elsevier Science Publishers, Amsterdam, NL.
B.M. Kim, etl.: "Efficient hydrolysis of beta-aminosulfamic acids using a Lewis acid and a thiol for the synthesis of 2,3-diaminopropanoate derivatives" Tetrahedron Letters, vol. 39, No. 30, Jul. 23, 1998, pp. 5381-5384, XP004123239 Elsevier Science Publishers, Amsterdam, NL.
S.B. Cohen, et al.: "Synthesis of S-linked glycosyl amino acids in aqueous solution with unprotected carbohydrates" Organic Letters, vol. 3, No. 3, Feb. 8, 2001, pp. 405-407, XP002182281 American Chemical Society, Washington, DC, US.
J.E. Bladwin, et al.: "Cyclic sulphamidates: new synthetic precursors for beta-functionalised alpha-amino acids" Tetrahedron Asymmetry, vol. 1, No. 12, 1990, pp. 881-884, XP002182282 Elsevier Science Publishers, Amsterdam, NL.
K.B. Wiberg: "Organic Syntheses, vol. 49" 1969, John Wiley and Sons, New York, NY, US XP002182283.
A.H. Blatt: "Organic Syntheses, Collective vol. 2" 1946, John Wiley and Sons, New York, NY, US XP002182284.
W.T. Hoeve et al.: "The Design of Resolving Agents. Chiral Cyclic Phosphoric Acids" Journal of Organic Chemistry, vol. 50, pp. 4508-4514, 1985 American Chemical Society, Washington, DC, US.
A. Mravik et al.: "Coordination-Mediated Optical Resolution of Carboxylic Acids with O,O'-Dibenzoyltartaric Acid" Angew. Chem. Int. Ed. Engl., pp. 1534-1536, 1997, 36 No. 13 14, VCH Verlagsgesellschaft mbH Weinheim, 1997.

* cited by examiner

*Primary Examiner*—Rei-tsang Shiao
(74) *Attorney, Agent, or Firm*—Hoffman & Baron LLP

(57) ABSTRACT

The invention relates to the use of chiral sulfamic acids as resolving agents, the sulfamic acid having the formula $(R_1,R_2)N-SO_3H$, wherein: $R_1$ and $R_2$, being the same or different, represent a hydrogen atom or a $C_1$-$C_{30}$ linear, branched or cyclic (hetero)-aliphatic or (hetero)-aromatic group, provided that $R_1$ and $R_2$ are not both hydrogen and that at least one of the $R_1$ and $R_2$ groups is chiral. Further, methods for resolving enantiomeric mixtures are disclosed.

21 Claims, No Drawings

USE OF SULFAMIC ACIDS AS RESOLVING AGENT

This application is a 371 of PCT/EP02/06321 filed on Jun. 7, 2002.

FIELD OF THE INVENTION

The invention relates to the use of chiral sulfamic acids as resolving agent for resolving an enantiomeric mixture, in particular a mixture of basic enantiomers, and to methods for resolving such enantiomeric mixtures.

BACKGROUND OF THE INVENTION

The term "enantiomeric mixture" is known in the art and is understood to mean a mixture of two enantiomers.

The term "resolving enantiomers" is understood in the art to mean the increase of the relative amount of a particular enantiomer in an enantiomeric mixture. Such a resolving method can be used to obtain an enantiomerically pure compound from an enantiomeric mixture. The term "resolving agent" used herein is understood to mean an agent that can be used for resolving enantiomers.

Resolving methods, known in the art are based on preferential crystallisation of diastereomeric salts, formed by a reaction of the resolving agent with the enantiomeric compounds in the mixture. Diastereomeric salts are known to have different physical properties, such as crystallisation characteristics; it is known in the art to separate diastereomeric salts from one another based on the said different characteristics, by choosing the proper conditions therefor. Ideally, only the salt of one enantiomeric form of the enantiomeric compound of the mixture precipitates under the chosen conditions, whereas the salts of the other enantiomer remain in solution. Said precipitate can be further purified, resulting in an enantiomerically enriched, or enantiomerically pure compound. Instead of, or in addition to the precipitated fraction, the liquid fraction, the so-called "mother liquor" can be used for the purification of the non-precipitated salt, comprising the antipodic enantiomer of the mixture in enantiomerically enriched form. Herein, an enantiomer is deemed to be "enantiomerically enriched" when the said enantiomer is present in a higher molar amount than the other (antipodic) enantiomer.

Resolution of racemic compounds through formation and separation of diastereomeric salts is an important technology for the preparation of enantiopure products on an industrial scale. The finding of a suitable resolving agent is however, often, trial and error.

In the art, carboxylic acids are known as resolving agents for resolving a mixture of basic enantiomers; however, such compounds have a relatively weak acidity, resulting in limiting salt formation, which is particularly problematic for resolving weak basic compounds.

Further, 10-camphorsulfonic acid is known as resolving agent for basic enantiomeric mixtures, see Stereochem. Org. Compounds, E. L. Eliel, S. H. Wilen, Wiley Interscience, N.Y., U.S.A., 1994, pp. 322-337. However, the diversity in resolving agents, in particular in resolving weak basic enantiomers, in limited.

SUMMARY OF THE INVENTION

According to the invention, it is now found that chiral sulfamic acids having an enantiomeric purity of at least 90% of formula (I):

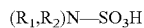

$$(R_1, R_2)N—SO_3H \qquad (I)$$

wherein:
$R_1$ and $R_2$, being the same or different, are selected from the group consisting of:
a hydrogen atom,
a linear, branched or cyclic alkyl or heteroalkyl group, being optionally substituted, or
an aromatic or heteroaromatic group, being optionally substituted, provided that $R_1$ and $R_2$ are not both hydrogen and that at least one of the $R_1$ and $R_2$ groups is chiral, have optimal and surprising properties rendering these compounds highly suitable for use as resolving agent for resolving a mixture of enantiomers, resulting in efficient resolution of mixtures of enantiomeric compounds.

The said sulfamic acids have a stronger acidity than corresponding carboxylic acids and will therefore have an increased potency for salt formation, particularly with weakly basic compounds. Thus the current method provides a significant enhancement in diversity.

DETAILED DESCRIPTION OF THE INVENTION

The term "enantiomeric purity of at least 90%" means that, on a molar basis, at least 95% of the sulfamic acid has the same stereochemic conformation; this means that less than 5% of the sulfamic acid is of the antipodic stereochemic conformation. This can be derived from the known formula for enantiomeric purity $$[(A-B)/(A+B)] \times 100\%,$$

wherein A and B stand for each of the enantiomers respectively. It is to be noted that the maximum obtainable resolution of the enantiomers in the mixture corresponds to the enantiomeric purity of the resolving agent; this means that when the resolving agent has an enantiomeric purity of 95%, the maximum obtainable resolution of the enantiomers will be 95%.

Sulfamic acids as such and the preparation thereof from amines are known in the art; U.S. Pat. No. 2,933,513 describes the preparation of (salts of) testosterone sulfamic acids. These compounds are used as water-soluble analogues of testosterone. A. G. Lloyd, et al. (Biochemical Journal 92, 1964, 68-72) discloses the synthesis of labeled sulfamic acids of D-glucosamine for metabolism studies. S.-K. Chung, et al. (Tetrahedron 54, 1998, 15899-15914) describe the synthesis of sulfamic acid steroid derivatives for use as antifungal agents. M. L. Wolfrom, et al. (Journal of the American Chemical Society 79, 1957, 5043-5046) disclose the synthesis of D-glucose derivatives containing a sulfamic acid group by reaction of D-glucosamine free base with $SO_3$-pyridine complex. This unit is present in heparin. M. H. Payne, et al. (Journal of Medicinal Chemistry 34, 1991, 1184-1187) describe the effect of sulfation in hirudin and hirudin PA related anticoagulant peptides as part of a structure activity relationship (SAR) study. Also, the synthesis of sulfamic acid derivatives of these peptides is given. R. Crosstick, et al. (Tetrahedron 40, 1984, 427-431) describe the synthesis of nucleoside analogues acting as antimetabolites (e.g. antiviral agents). One of the synthesised compounds is a sulfamic acid prepared from an amine and $SO_3$-triethylamine complex. I. Marle, et al. (Journal of Chromatography 586, 1991, 223-248) disclose a new chiral stationary phase for high-performance liquid chromatography based on cellulase. One of the solute structures is alfa-phenylethyl sulfamic acid. B. M. Kim, et al. (Tetrahedron letters 39, 1998, 5381-5384) describe new hydrolysis conditions for alfa-aminosulfamic acids, resulting in the formation of chiral diamines. These compounds are important building blocks in the synthesis of enzyme inhibitors. S. B. Cohen, et al. (Organic Letters 3, 2001, 405-407) present the synthesis of S-linked glycoconjugates via opening of a cyclic sulfamidate with 1-thio sugars and hydrolysis of the resulting sulfamic acids. J. E. Baldwin, et al. (Tetrahedron Asymmetry 1, 1990, 881-884) describe the nucleophilic opening of cyclic sulfamidates and subsequent hydrolysis of the in situ formed sulfamic acid is described.

When the sulfamic acid comprises, as R1 or R2, or both, an alkyl group, the alkyl group is preferably $C_1$-$C_{30}$ alkyl group; if the said alkyl group comprises a hetero atom, the said hetero atom is preferably selected from N, P, O and S.

When the sulfamic acid comprises, as R1 or R2, or both, an aromatic or heteroaromatic group, the said group preferably has 3-30 C-atoms; in case the said aromatic group is a heteroaromatic group, the hetero atom is preferably selected from N, P, O and S.

It is nevertheless observed that the above enumerations are not limitative; $R_1$ and $R_2$ can also represent other groups, provided that the sulfamic acid is still chiral.

Preferably, the sulfamic acid has an enantiomeric purity of at least 95%, more preferably of at least 99% or more. Most preferably, the sulfamic acid is homochiral. As outlined above, the resolution of the enantiomers in the mixture is dependent on the enantiomeric purity of the resolving agent; therefore, it is highly preferred for the sulfamic acid to be as enantiomerically (i.e. chirally) pure as possible.

As the salt formation of the sulfamic acid an the enantiomers in the mixture is an acid-base reaction, the enantiomers in the mixture to be resolved are preferably basic enantiomers. The enantiomers should at least be capable of being susceptible to an acid-base reaction with sulfamic acid to form the diastereomeric salts. The basic enantiomers are preferably amines.

According to the invention sulfamic acid can be used advantageously to resolve both racemic and non-racemic mixtures, e.g. wherein the molar ratio between both enantiomers is 1:10.

The invention further relates to a method for resolving a mixture of enantiomers B, comprising the steps of:
a) reacting in a liquid medium said mixture with a chiral sulfamic acid having an enantiomeric purity of at least 90% of formula (I):

as defined above, to obtain diastereomeric salts of formula (IV):

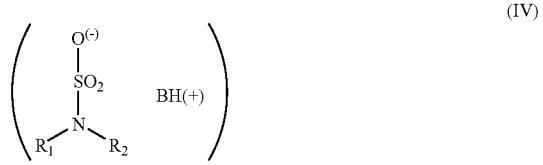

resulting in preferential crystallization of either the p- or the n-diastereomeric salt,
b) recovering the crystallized salt obtained in step a),
c) treating the recovered crystallized salt of b) with a base to obtain the compound B in an enantiomerically enriched form, and, optionally,
d) recovering the sulfamic acid from c).

This process is schematically represented as follows:

Scheme 1:

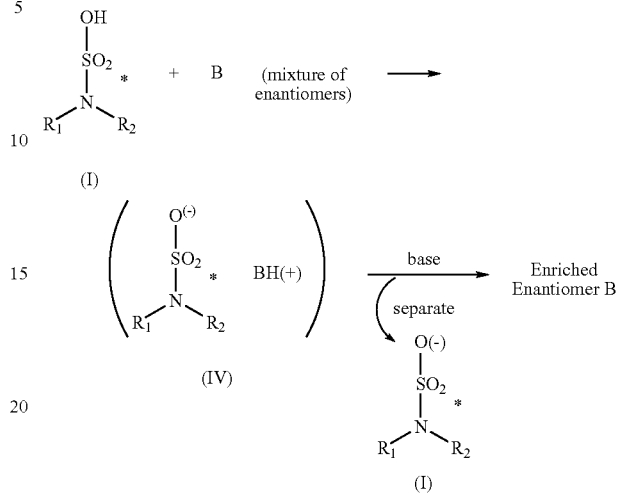

According to the above method, enantiomeric mixtures can be resolved via intermediacy of sulfamate formation; in step a), the enantiomeric mixture is reacted with a sulfamic acid forming diastereomeric sulfamate salts through an acid-base reaction. Proper reaction conditions are known in the art; any skilled person will be aware of finding the conditions to conduct such a reaction. By this reaction, the p- or n-form of the diastereomeric salts crystallise and precipitate preferentially, as is outlined above, therewith leaving the remaining enantiomeric form, the antipode, in solution. The skilled person will be aware of suitable reaction conditions to obtain the envisaged preferential crystallisation. Subsequently, the crystallised salt is recovered from the mixture by purification methods, known in the art. The recovered crystallised salt comprises the required enantiomer in enriched form. To obtain the enantiomer in the original form, the salt is treated with a base, so that the original enantiomer is released. It is to be understood that hereto, the said base should preferably be a stronger base than the enantiomer in the salt. Said enriched enantiomer can be further purified as known in the art. Optionally, the sulfamic acid is recovered from the mixture by e.g. acidification of the mixture; an example of a suitable recovery is by ion exchange and subsequent freeze drying. The recovered sulfamic acid can be reused.

It is also possible to recover the envisaged enantiomer from the mother liquor, in case the salt of the said enantiomer remains in solution, and the salt of the antipode crystallises. In such a case, the mother liquor is enantiomerically enriched by removal of the precipitated crystals of the salt of the antipode. If both enantiomers are to be purified, both the salt crystals and the solubilised salt can be used for further purification of the respective enantiomers. Thus, in addition to or instead of steps b) and c) the diastereomeric salts from the liquid can be recovered and treated with a base to obtain compound B in an enantiomerically enriched form.

In order to obtain optimal resolution, as outlined above, the sulfamic acid has an enantiomeric purity of least 90%, preferably at least 95%, more preferably at least 99% or more and most preferably being homochiral. The best resolution is obtained when the sulfamic acid is as chirally pure as possible.

Preferably, as outlined above, the enantiomers B are basic enantiomers, preferably amines.

In a very special embodiment of the invention, the enantiomeric compounds of the mixture are amines, and the $(R_1,R_2)N$-moiety of the sulfamic acid used as resolving agent is stereochemically identical to the $(R_1,R_2)N$-moiety of one of the amines of the enantiomeric mixture. This is particularly advantageous when the n-salt of the sulfamic acid and the enantiomer crystallises. In that case, the crystallised salt constitutes of two chirally identical amine moieties that both can be purified; first, the n-salt is treated with a base as outlined above, resulting in release of the envisaged enantiomeric amine; second, the sulfamic acid can be recovered and treated, e.g. with an acid, to remove the $SO_3$ moiety therefrom resulting in stereochemically the same amine as released from the salt, therewith duplicating the yield. Thus, the purified product originates both from the enantiomeric mixture and from the resolving sulfamic acid. As outlined above, it is also possible to obtain the envisaged enantiomer in case the n-salt remains in solution, by recovering the said salt from the solution. Thereto, the mixture of basic enantiomers comprise an enantiomeric mixture of amines of formula (II):

  (II), wherein R1 and R2 are as above, and wherein the $(R_1,R_2)$ N-moiety of the sulfamic acid of step a) is identical to at least one of the amines in the said enantiomeric mixture; in that case, "B" in the above scheme is

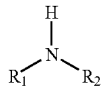  (II)

Very interestingly, it has also been found that the use of sulfamic acid as resolving agent enables the resolution of enantiomeric mixtures of amines of formula (II), as defined above, by first converting the said amines in an enantiomeric mixture of sulfamic acids, and by subsequent resolution of the thus formed enantiomeric sulfamic acid mixture with a suitable basic resolving agent; thereto the invention provides a method for resolving an enantiomeric mixture of amines of formula (II):

  (II)

wherein $R_1$ and $R_2$ are as defined above, comprising the steps of:

1) reacting the said amines with a suitable reagent to obtain an enantiomeric mixture of corresponding sulfamic acid having formula (I) as defined above,
2) reacting the sulfamic acid of step 1) with a chiral basic resolving agent A having an enantiomeric purity of at least 90% to obtain diastereomeric salts of formula (V)

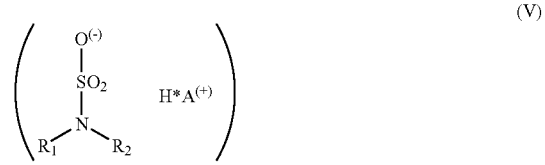

resulting in preferential crystallisation of either the p- or the n-diastereomeric salt,
3) recovering the crystallised salt obtained in step 2),
4) treating the recovered crystallised salt of step 3), with an acid to obtain the sulfamic acid of formula (I) in an enantiomerically enriched form,
5) recovering the amine of formula (II) from the sulfamic acid obtained in step 4) by removal of $SO_3$, and, optionally,
6) recycling the resolving agent A from step 4).

The above method is illustrated in the reaction scheme below:

Scheme 2:

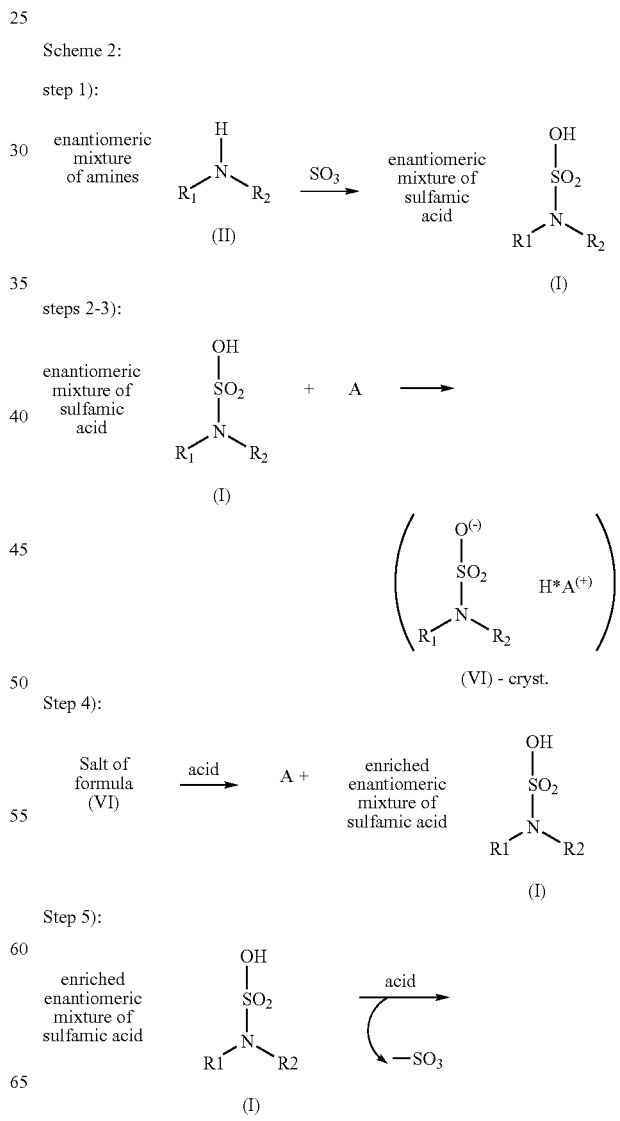

enriched amine enantiomers 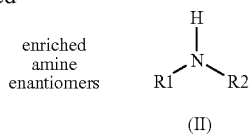

(II)

Virtually all commercially available chiral amines can be used in the above process, for example, (R)-1-(4-nitrophenyl)ethylamine hydrochloride, (+)-dehydroabiethylamine, (S)-2-amino-1,1-diphenyl propanol, D-phenylalaninol, L-(−)-α-amino-ε-caprolactam, (R)-(−)-1-amino-2-propanol, (R)-(+)-1-(1-naphthyl)ethylamine, (R)-(+)-1-(2-naphthyl)ethylamine, (R)-(+)-1-(4-bromophenyl)ethylamine, (R)-(+)-α-methylbenzylamine, (S)-(−)-1-(1-naphthyl)ethylamine, (S)-(−)-1-(2-naphthyl)ethylamine, (S)-(−)-1-(4-bromophenyl)ethylamine, (S)-(−)-α-methylbenzylamine, (S)-(+)-1-amino-2-propanol, (R)-(+)-bornylamine, (R)-(−)-phenylglycinol, (S)-(+)-phenylglycinol, D-(+)-phenylalaninol, L-(−)-phenylalaninol, (1S,2S)-(+)-2-amino-3-methoxy-1-phenyl-1-propanol, (−)-cis-myrtanylamine, D-(+)-norephedrine, L-(−)-norephedrine, (1R,2R)-(−)-2-amino-1-phenyl-1,3-propanediol, (1S,2S)-(+)-2-amino-1-phenyl-1,3-propanediol, (R)-(−)-1-aminoindan, (S)-(+)-1-aminoindan, (−)-isopinocamphenylamine, (+)-isopinocamphenylamine, (1R,2S)-(−)-cis-1-amino-2-indanol, (1S,2R)-(+)-cis-1-amino-2-indanol, (S)-2-phenylglycine methyl ester hydrochloride, (S)-2-phenylglycine methyl ester hydrochloride, (−)-L-phenylalanine benzyl ester, (R)-1-(3-methoxyphenyl)ethylamine, (S)-1-(3-methoxyphenyl)ethylamine, (R)-1-(4-methoxyphenyl)ethylamine, (S)-1-(4-methoxyphenyl)ethylamine, (1R,2S)-(+)-cis-[2-(benzylamino)cyclohexyl]methanol, (−)-bis[(S)-1-phenylethyl amine hydrochloride, (−)-ephedrine, (+)-bis-[(R)-1-phenylethyl]amine hydrochloride, (+)-ephedrine hydrochloride, (1S,2R)-(−)-cis-[2-(benzylamino)cyclohexyl]methanol, (R)-benzyl-1-(1-naphthyl)ethylamine hydrochloride, (S)-1-(4-nitrophenyl)ethylamine hydrochloride, (S)-benzyl-1-(1-naphthyl)ethylamine hydrochloride, (R)-(+)-N-benzyl-1-phenylethylamine, (R)-(+)-N-methyl-1-phenylethylamine, (1R,2S)-(−)-N-methylephedrine, brucine, quinine, (−)-strychnine, cinchonidine, cichonine, quinidine, (R)-(+)-N,N-dimethyl-1-phenylethylamine, (S)-(−)-N,N-dimethyl-1-phenylethylamine, D-arginine, D-aspartic acid, D-glutamic acid, D-valine, L-aspartic acid, L-glutamic acid, L-valine.

Preferably, the suitable reagent to be used in the above process, is chlorosulfonic acid, sulfur trioxide, adducts of sulfur trioxide, such as in particular sulfur trioxide pyridine complex, sulfur trioxide dimethylformamide complex; also virtually any other adduct of sulfur trioxide can be used for the preparation of the envisaged sulfamic acids.

Because many starting amines are inexpensive reagents, and for the conversion thereof to sulfamic acids inexpensive reagents can be used, a basis for the large-scale use of sulfamic acids in diastereomer mediated resolutions is provided. The skilled person is aware of suitable reaction conditions for the preparation of the envisaged sulfamic acids.

Suitable basic resolving agents are known in the art, and can e.g. be chosen from the above-mentioned list of chiral amines.

In step 4), an acid should be used that is stronger than the sulfamic acid of the crystallised salt.

Treatment of a sulfamic acid to obtain the corresponding amine, the above step 5), are known in the art; preferably, step 5) comprises treatment of the sulfamic acid with chemical or thermal means, preferably by treatment with a hydrohalogenic acid, preferably hydrochloric acid. Steps 4) and 5) may preferably be combined by a single acid treatment. In addition to the above acids, the skilled person will be aware of suitable acids, such as e.g. sulfuric acid and nitric acid.

As outlined above, it is also possible to recover the envisaged enantiomer from the mother liquor, in case the salt of the said enantiomer remains in solution, and the salt of the antipode crystallises. In such a case, the mother liquor is enantiomerically enriched by removal of the precipitated crystals of the salt of the antipode. If both enantiomers are to be purified, both the salt crystals and the solubilised salt can be used for further purification of the respective enantiomers. Thus, in addition to or instead of steps 3) and 4) the diastereomeric salts from the liquid can be recovered and treated with an acid to obtain the sulfamic acid in an enantiomerically enriched form.

In a very special embodiment of the invention, the basic resolving agent is an amine, having a $(R_1,R_2)N$— moiety being stereochemically identical to the $(R_1,R_2)N$— moiety of one of the sulfamic acid enantiomers of the enantiomeric mixture. This is particularly advantageous when the n-salt of the sulfamic acid enantiomer and the resolving amine crystallises. In that case, the crystallised salt constitutes of two chirally identical amine moieties that both can be purified; first, the n-salt is treated with an acid as outlined above, resulting in release of the envisaged enantiomeric sulfamic acid; the amine is subsequently released from the said sulfamic acid by removal of the $SO_3$ moiety therefrom, e.g. with an acid. Second, the resolving amine, being stereochemically identical to that of the said sulfamic acid is recovered from the salt, resulting in duplication of the yield. Thus, the purified product originates both from the enantiomeric sulfamic acid mixture and from the resolving amine. As outlined above, it is also possible to obtain the envisaged enantiomer in case the n-salt remains in solution, by recovering the said salt from the solution. Thus, the basic resolving agent A preferably comprises an enantiomer of the amines to be resolved, which amines are first converted to the corresponding sulfamic acid.

According to the method according to the invention, it is also possible to resolve an enantiomeric mixture of sulfamic acids, without first converting an amine into the corresponding sulfamic acid; in that case, any enantiomeric mixture of sulfamic acids may be used and resolved (i.e. be enriched in one of the enantiomers of the mixture). Also, a further removal of $SO_3$ from the obtained enantiomerically enriched sulfamic acid is not necessary. Thus, the above steps 1) and 5) are not performed according to this embodiment of the invention.

As outlined above, it is highly preferred to use a resolving agent that is chirally as pure as possible, resulting in chirally highly enriched enantiomers, or even to chirally pure enantiomers (i.e. having a chiral purity of 95-100%, preferably 99-100%). Thereto, the resolving agent has an enantiomeric purity of at least 90%, preferably of at least 95%, more preferably of at least 99%; the resolving agent is most preferably homochiral.

Preferably, the molar ratio of the resolving agent:enantiomers in the mixture is substoichiometric and preferably 0.5 eq, as explained by Pope and Peachey in their method of half quantities, and disclosed in Enantiomers, Racemates and Resolutions, Wiley and Sons, New York (1981), pp. 309-313, herein incorporated by reference.

In an attractive embodiment of the invention, the enantiomeric mixture to be resolved is preferably a racemic mixture, in particular when substoichiometric amounts of resolving agent are used (see Pope and Peachy, supra).

The invention is now further illustrated by non-limitative examples.

EXAMPLE 1

Preparation of D-phenylalaninol sulfamic acid 500 mg (3.31 mmol) D-phenylalaninol was dissolved in 10 ml of demi-water. The pH of the mixture was adjusted to pH 9.5-10.0 via addition of an aqueous 1.0 N NaOH solution. 659 mg (3.64 mmol) of sulfur trioxide pyridine complex was added in small portions over a period of 0.5 h with constant addition of 1.0 N NaOH solution to maintain a pH of 9.5-10.0. After the reaction was complete the reaction mixture was concentrated to remove the pyridine. Ethanol was added and the formed precipitate was removed by filtration and discarded. Acetone was added and the product precipitated from the solution. Filtration yielded 537 mg (2.32 mmol) of the sodium salt of D-phenylalaninol sulfamic acid (70%).

Next, 92 mg (0.36 mmol) of the sodium salt of D-phenylalaninol sulfamic acid was dissolved in 5 ml demineralized water. 3 ml of a suspension of Dowex-H$^+$ in demineralized water was added and stirred for 5 min. The mixture was filtered, the resin was rinsed 4 times with 5 ml of demineralized water and the collected aqueous filtrate was freeze-dried. 85 mg (0.36 mmol) of D-phenylalaninol sulfamic acid was obtained after freeze-drying.

EXAMPLE 2

Resolution of racemic α-methylbenzylamine 80 mg (0.34 mmol) of D-phenylalaninol sulfamic acid was dissolved in 15 ml ethanol after which 43 mg (0.35 mmol) of racemic α-methylbenzylamine dissolved in 2 ml ethanol was added. The solvent was evaporated to a total volume of 3 ml and cooled down to accelerate crystallisation. After crystallisation both mother liquor and crystals were analysed by HPLC on a chiral ODH-column (eluent hexane: isopropylalcohol 90:10) to determine the relative amount of (S)- and (R)-α-methylbenzylamine. HPLC analysis showed enantiomeric enrichment of both the crystals and the mother liquor.

EXAMPLE 3

Preparation of (D)-1-(-3-methoxyphenyl)ethyl sulfamic acid and resolution of racemic α-methylbenzylamine 1.17 g (7.73 mmol) (D)-1-(-3-methoxyphenyl)ethyl amine was added dropwise to a suspension of 1.32 g (8.63 mmol) sulfur trioxide N,N-dimethylformamide complex in 15 ml of THF. After stirring for 10 min. TLC-analysis showed complete disappearance of primary amine (ninhydrine colouring). After evaporation of the solvents the sulfamic acid was obtained as a clear oil.

87 mg (0.38 mmol) of the sulfamic acid of (D)-1-(-3-methoxyphenyl)ethyl amine was dissolved in 1 ml of acetone and 48 mg (0.40 mmol) of racemic α-methylbenzylamine in 1 ml acetone was added. Within an hour crystals were formed and HPLC analysis showed enantiomeric enrichment of both the crystals and the mother liquor.

What is claimed is:

1. A method for resolving an enantiomeric mixture of enantiomers B, wherein enantiomers B are basic enantiomers mixture of amines of formula (II), (R1,R2)N—H         (II)

comprising the steps of:
   a) reacting in a liquid medium said enantiomeric mixture of basic enantiomers with a chiral sulfamic acid having an enantiomeric purity of at least 90% of formula (I):

(R1,R2)N—SO3H         (I)

wherein:
R1 and R2, being the same or different, are selected from the group consisting of:
   hydrogen,
   a linear, branched or cyclic alkyl or heteroalkyl group, being optionally substituted, or
   an aromatic, being optionally substituted, provided that R1 and R2 are not both hydrogen and that at least one of the R1 and R2 groups is chiral, to obtain diastereomeric salts of formula (IV):

wherein B is enantiomers mixture of amines of formula (II),
resulting in preferential crystallization of either the p- or the n-diastereomeric salt,
   b) recovering the crystallized salt obtained in step a),
   c) treating the recovered crystallized salt of b) with a base to obtain the enantiomers B in an enantiomerically enriched form, and, optionally,
   d) recovering the sulfamic acid from c).

2. The method according to claim 1, wherein in addition to or instead of steps b) and c) the diastereomeric salts from the liquid are recovered and treated with a base to obtain enantiomers B in an enantiomerically enriched form.

3. The method according to claim 2, wherein the sulfamic acid has an enantiomeric purity of at least 95%, and most preferably of at least 99% or more.

4. The method according to claim 1, wherein the mixture of enantiomers B is an enantiomeric mixture of amines of formula (II):

(R1,R2)N—H         (II),

wherein R1 and R2, being the same or different, are selected from the group consisting of:
   hydrogen,
   a linear, branched or cyclic alkyl or heteroalkyl group, being optionally substituted, or
   an aromatic group, being optionally substituted, provided that R1 and R2 are not both hydrogen and that at least one of the R1 and R2 groups is chiral, and wherein the (R1,R2)N— moiety of the sulfamic acid of step a) is identical to at least one of the amines in the said enantiomeric mixture.

5. Method according to claim 4, further comprising step:
e) removing the $SO_3$ moiety of the sulfamic acid, recovered in step d) to obtain the amine of formula (II).

6. A method for resolving an enantiomeric mixture of amines of formula (II):

(R1,R2)N—H     (II)

wherein R1 and R2, being the same or different, are selected from the group consisting of:
hydrogen,
a linear, branched or cyclic alkyl or heteroalkyl group, being optionally substituted, or
an aromatic group, being optionally substituted, provided that R1 and R2 are not both hydrogen and that at least one of the R1 and R2 groups is chiral, comprising the steps of:

1) reacting the said amines with a suitable reagent to obtain an enantiomeric mixture of corresponding sulfamic acid having formula (I):

(R1,R2)N—SO3H     (I)

wherein:
R1 and R2, being the same or different, are selected from the group consisting of:
hydrogen,
a linear, branched or cyclic alkyl or heteroalkyl group, being optionally substituted, or
an aromatic group, being optionally substituted, provided that R1 and R2 are not both hydrogen and that at least one of the R1 and R2 groups is chiral, 2) reacting in a liquid medium the sulfamic acid of step 1) with a chiral basic resolving agent A having an enantiomeric purity of at least 90% to obtain diastereomeric salts of formula (V)

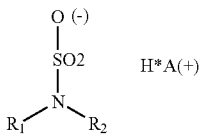

(V)

resulting in preferential crystallization of either the p- or the n-diastereomeric salt, 3) recovering the crystallised salt obtained in step 2),
4) treating the recovered crystallised salt of step 3), with an acid to obtain the sulfamic acid of formula (I) in an enantiomerically enriched form,
5) recovering the amine of formula (II) from the sulfamic acid obtained in step 4) by removal of $SO_3$, and, optionally, 6) recovering the resolving agent A from step 4).

7. The method according to claim 6, wherein in addition to or instead of steps 3) and 4) the diastereomeric salts from the liquid are recovered and treated with an acid to obtain the sulfamic acid in an enantiomerically enriched form.

8. The method according to claim 6, wherein the reagent of step 1) comprises chlorosulfonic acid, sulfur trioxide, adducts of sulfur trioxide, sulfur trioxide pyridine complex, sulfur trioxide dimethylformamide complex or a combination of two or more thereof.

9. The method according to any of the claim 5, wherein step e) comprises treatment of the sulfamic acid with chemical or thermal means.

10. The method according to any of the claim 6, wherein the basic resolving agent A comprises an enantiomer of the amines to be resolved.

11. The method for the resolution of an enantiomeric mixture of sulfamic acids having formula (I) as defined in claim 6, comprising steps 2), 3), 4) and optionally step 6) of claim 12.

12. The method according to claim 1, wherein the resolving agent has an enantiomeric purity of at least 95%.

13. The method according to claim 1, wherein the molar ratio of resolving agent:entantiomers in the mixture to resolving agent is used in a substoichiometric amount and most preferably at 0.5 eq.

14. The method according to claim 1, wherein the mixture of enantiomers is a racemic mixture.

15. The method according to claim 5, wherein step e) comprises treatment of the sulfamicacid with a hydrohalogenic acid.

16. The method according to claim 6, wherein step 5 comprises treatment of the sulfamic acid with chemical or thermal means.

17. The method according to claim 6, wherein step 5 comprises treatment of the sulfamicacid with a hydrohalogenic acid.

18. The method according to claim 6, wherein the resolving agent A has an enantiomeric purity of at least 99%.

19. The method according to claim 1, wherein the sulfamic acid has an enantiomeric purity of at least 99%.

20. The method according to claim 6, wherein the molar ratio of resolving agent A: entantiomers in the mixture to resolving agent is used in a substoichiometric amount and most preferably at 0.5 eq.

21. The method according to claim 6, wherein the mixture of enantiomers is a racemic mixture.

* * * * *